(12) United States Patent
Brahm

(10) Patent No.: US 11,224,616 B1
(45) Date of Patent: *Jan. 18, 2022

(54) PLATELET-RICH PLASMA DERIVED FROM HUMAN UMBILICAL CORD BLOOD

(71) Applicant: BioDlogics LLC, Cordova, TN (US)

(72) Inventor: Timothy R. Brahm, Germantown, TN (US)

(73) Assignee: BIODLOGICS, LLC, Cordova, TN (US)

( * ) Notice: Subject to any disclaimer, the term of this patent is extended or adjusted under 35 U.S.C. 154(b) by 162 days.

This patent is subject to a terminal disclaimer.

(21) Appl. No.: 16/007,246

(22) Filed: Jun. 13, 2018

Related U.S. Application Data

(63) Continuation of application No. 14/196,331, filed on Mar. 4, 2014, now Pat. No. 10,016,459.

(60) Provisional application No. 61/778,527, filed on Mar. 13, 2013.

(51) Int. Cl.
| | | |
|---|---|---|
| *A61K 35/19* | (2015.01) | |
| *C12N 5/073* | (2010.01) | |
| *A61K 35/50* | (2015.01) | |
| *A61K 35/51* | (2015.01) | |

(52) U.S. Cl.
CPC .............. *A61K 35/19* (2013.01); *A61K 35/50* (2013.01); *A61K 35/51* (2013.01); *C12N 5/0605* (2013.01)

(58) Field of Classification Search
CPC ......... A61K 35/19; A61K 35/50; A61K 35/51
See application file for complete search history.

(56) References Cited

U.S. PATENT DOCUMENTS

| | | | |
|---|---|---|---|
| 3,409,016 | A | 11/1968 | Foley |
| 5,036,056 | A | 7/1991 | Kludas |
| 7,727,550 | B2 | 6/2010 | Siegal |
| 7,871,646 | B2 | 1/2011 | Ghinelli |
| 8,071,135 | B2 | 12/2011 | Liu |
| 8,182,840 | B2 | 5/2012 | Tseng |
| 8,182,841 | B2 | 5/2012 | Tseng |
| 8,187,639 | B2 | 5/2012 | Tseng |
| 8,258,117 | B2 | 9/2012 | Hoemann |
| 8,529,957 | B2 | 9/2013 | Turzi |
| 2003/0235580 | A1 | 12/2003 | Zhang |
| 2004/0057938 | A1 | 3/2004 | Ghinelli |
| 2006/0004189 | A1 | 1/2006 | Gandy |
| 2006/0142198 | A1 | 6/2006 | Gandy |
| 2007/0021762 | A1 | 1/2007 | Liu |
| 2007/0292401 | A1 | 12/2007 | Harmon |
| 2008/0050814 | A1 | 2/2008 | Allickson |
| 2010/0036503 | A1 | 2/2010 | Chen |
| 2011/0117171 | A1 | 5/2011 | Melican |
| 2012/0141595 | A1 | 6/2012 | Tseng |
| 2012/0171180 | A1* | 7/2012 | Abramson ............. A61K 35/16 424/93.72 |

FOREIGN PATENT DOCUMENTS

| | | | |
|---|---|---|---|
| EP | 0285370 | A2 | 10/1988 |
| WO | 06094247 | A2 | 9/2006 |
| WO | 07148346 | A2 | 12/2007 |
| WO | 09052132 | A1 | 4/2009 |
| WO | 11110948 | A2 | 9/2011 |
| WO | 12003377 | A2 | 1/2012 |

OTHER PUBLICATIONS

In 't Anker et al., Isolation of mesenchymal stem cells of fetal or maternal origin from human placenta. Stem Cells, vol. 22, No. 7 (Dec. 2004) pp. 1338-1345. (Year: 2004).*
Murphy et al., Adult and umbilical cord blood-derived platelet-rich plasma for mesenchymal stem cell proliferation, chemotaxis, and cryo-preservation. Biomaterials, vol. 33 (online Apr. 27, 2012) pp. 5308-5316. (Year: 2012).*
Sommeling et al., The use of platelet-rich plasma in plastic surgery: a systematic review. Journal of Plastic, Reconstructive & Anesthetic Surgery, vol. 66 (online Dec. 11, 2012) pp. 301-312. (Year: 2012).*
Anker, et al., "Isolation of mesenchymal stem cells of fetal or maternal origin from human placenta", Stem Cells, vol. 22, No. 7 (Dec. 2004), pp. 1338-1345.
Freshney, R.I., et al., "Primary culture", Culture of Animal Cell: A Manual of Basic Technique and Specialized Applications (Hoboken, NJ, John Wiley & Sons, Inc., 2010), pp. 163-186.
Haimov-Kochman et al., "Modification of the standard trizol-based technique improves the integrity of RNA isolated from RNaserich placetal tissue", Clinical Chemistry (2006), vol. 52, No. 1, pp. 159-160.
Iacono et al., "Effects of mesenchymal stem cells isolated from amniotic fluid and platelet-rich plasma gel on severe decubitus ulcers in a septic neonatal foal", Research in Veterinary Science, vol. 93 (online May 9, 2012), pp. 1439-1440.
Lee et al., "The effects of platelet-rich plasma derived from human umbilical cord blood on the osteogenic differentiation of human dental cells", In vitro Cell Development Biology, vol. 47 (2011), pp. 157-164.
Murphy, et al., "Adult and umbilical cord blood-derived platelet-rich plasma for mesenchymal stem cell proliferation, chemotaxis, and cryo-preservation", Biomaterials, vol. 33 (online Apr. 27, 2012), pp. 5308-5316.
News article on Innovota Research Foundation website entitled "Platelet Rich Plasma from Umbilical Cord Blood—Properties and Opportunities", posted on Dec. 28, 2010, available at: http://www.innovitaresearch.org/news/10122802.html, 2 pages.
Sommeling et al., "The use of platelet-rich plasma in plastic surgery: a systemic review", Journal of Plastic, Reconstructive & Anesthetic Surgery, vol. 66 (online Dec. 11, 2012), pp. 301-312.

* cited by examiner

*Primary Examiner* — Kara D Johnson
(74) *Attorney, Agent, or Firm* — Barnes & Thornburg LLP

(57) ABSTRACT

A wound or tissue healing composition and related treatment methods are provided. The wound or tissue healing composition includes an effective amount of a platelet-rich plasma aseptically recovered from umbilical cord and an effective amount of a human birth tissue material composition.

10 Claims, No Drawings

PLATELET-RICH PLASMA DERIVED FROM HUMAN UMBILICAL CORD BLOOD

CROSS-REFERENCE TO RELATED APPLICATIONS

This application is a continuation application of U.S. Ser. No. 14/916,331, filed on Mar. 4, 2014, which claims priority to U.S. Provisional Patent Application No. 61/778,527 filed Mar. 13, 2013, the contents of which are each incorporated herein in their entirety.

FIELD OF INVENTION

The present invention is directed to a platelet-rich plasma composed of aseptically recovered human umbilical cord blood, as well as uses thereof. Specifically, the invention provides compositions of platelet-rich plasma alone or in combination with a human birth tissue material composition for use in treating a wound or defect or for promotion of regeneration in diseased or damaged tissue. The invention also provides for cosmetic compositions of platelet-rich plasma alone or in combination with a human birth tissue material composition and/or an optional cosmetically acceptable carrier.

BACKGROUND OF INVENTION

Platelet-rich plasma as a clinical treatment for bone, muscle, tendon, and cartilage injury has gained significant popularity in the field of orthopedic sports medicine in recent years due to its integral role in accelerating the cellular response to injury in the tissue repair and regeneration processes. The healing potential of platelet-rich plasma preparations is largely attributed to its dense concentration of growth factors and cytokines derived from platelets.

Platelet-rich plasma may be defined as an autologous concentrate of platelets in a small volume of plasma. Currently, platelet-rich plasma is defined only by the absolute quantity of platelets in the preparation, and not by the presence of other components. Normal platelet counts in blood range from approximately 150,000 to 350,000/µL, whereas platelet-rich plasma is often defined as at least 1,000,000 platelets/µL suspended in plasma. To ensure that platelets are suspended and do not form a clot, platelet-rich plasma is derived from anti-coagulated blood.

Multiple studies have demonstrated the role of platelet-rich plasma in accelerating and facilitating improved response to injury. The theoretical basis for the use of platelet-rich plasma in tissue repair is that large numbers of platelets appear immediately at the site of tissue injury and release growth factors and cytokines, thereby initiating the wound healing process. Thus, the enhancement of healing by the placement of a supraphysiologic concentration of platelets at the site of tissue injury is supported by basic science.

Many of the cytokines and growth factors believed to be responsible for the effects of platelet-rich plasma are contained within the α-granules of platelets, including, but not limited to, platelet-derived growth factor (PDGF), transforming growth factor β (TGF-β), insulin-like growth factor 1 (IGF-1), insulin-like growth factor 2 (IGF-2), fibroblast growth factor (FGF), epidermal growth factor (EGF), vascular endothelial growth factor (VEGF), Interleukin 8 (IL-8), keratinocyte growth factor (KGF), connective tissue growth factor (CTGF), platelet-derived angiogenesis factor (PDAF), platelet-derived endothelial growth factor (PDEGF), epithelial cell growth factor (ECGF), osteocalcin, osteonectin, fibrinogen, vitronectin, fibronectin, and thrombospondin. Platelet activation triggers degranulation and release of these factors, which, in turn, stimulates wound healing by promoting such actions as: (i) inducement of proliferation and differentiation of various cell types (e.g., stem cell, osteoblast, epidermal cell); (ii) enhancement/ modulation of production of collagens and proteoglycans; and (iii) stimulation of angiogenesis.

Currently, treatment with platelet-rich plasma involves autologous use (e.g., the platelet-rich plasma is used to treat the individual from whom the blood was collected). Typically, a small amount of blood (usually 25-50 mL) is collected from the patient. Using centrifugation, the plasma, platelets and red blood cell components are separated and 3-5 mL of a platelet-rich fraction is extracted. This platelet-rich fraction may then be pre-activated with the clotting factor, thrombin, or directly injected back into the patient at the site of injury.

The present invention seeks to disclose human umbilical cord blood as an allogeneic source (e.g., from an individual other than the one receiving treatment) of platelet-rich plasma. Human umbilical cord blood is the blood that remains in the placenta and the attached umbilical cord after childbirth. The cord blood is composed of all of the elements found in whole blood, including red blood cells, white blood cells, plasma and platelets. Additionally, human umbilical cord blood is also rich in stem cells (e.g., hematopoietic stem cells, mesenchymal stem cells, multipotent adult progenitor cells, unrestricted somatic stem cells, endothelial progenitor cells). Thus, human umbilical cord blood is a viable alternative source for platelet-rich plasma preparations.

SUMMARY OF INVENTION

The present invention provides a platelet-rich plasma composed of aseptically recovered umbilical cord blood. In one embodiment, the umbilical cord blood is of human origin. The invention also provides a wound or tissue healing composition comprising an effective amount of the platelet-rich plasma as described herein admixed with an effective amount of a human birth tissue material composition. The human birth tissue material composition can comprise one or more of the components of the placental organ, including, but not limited to, placental globe, the umbilical cord, the chorionic membrane, the amniotic membrane, the amniotic fluid, and other gelatins, cells, and extracellular material of the placental organ.

In a preferred embodiment, a wound or tissue healing composition is provided. The wound or tissue healing composition can include an effective amount of a platelet-rich plasma described herein admixed with an effective amount of a human birth tissue material composition. The birth tissue material composition may include one or more of the components of the placental organ. Exemplary placental organ components include the placental globe, the umbilical cord, the chorionic membrane, the amniotic membrane, the amniotic fluid, and other placental gelatins, cells, and extracellular material and combinations thereof.

According to one embodiment, a method of treating a wound or defect is provided. The method includes the steps of preparing a platelet-rich plasma as described herein; or preparing a wound or tissue healing composition as described herein; and administering an effective amount of either the platelet-rich plasma or the wound or tissue healing composition onto or into the wound or defect. In one aspect, the wound includes a diabetic ulcer, decubitus ulcer, venous leg ulcer, arterial leg ulcer, cutaneous ulcer, or a wound arising on or around a soft tissue, connective tissue (e.g., cartilage, tendon, ligament), adipose tissue, bone, nerve, organ, vascular tissue, muscle, spinal cord, oral cavity, ocular surface, or a combination thereof. According to one aspect, the defect includes a soft tissue defect or bone void.

According to one embodiment, a method of promoting regeneration of a diseased or damaged tissue is provided. The method includes the steps of preparing a platelet-rich plasma as described herein; or preparing a wound or tissue healing composition as described herein; and administering an effective amount of either the platelet-rich plasma or the wound or tissue healing composition onto or into the diseased or damaged tissue. In one aspect, the diseased or damaged tissue includes, but is not limited to, soft tissue, connective tissue (e.g., cartilage, tendon, ligament), adipose tissue, bone, nerve, organ, vascular tissue, muscle, spinal cord, oral cavity, ocular surface, or a combination thereof.

In one aspect of the invention, a cosmetic composition is provided. The cosmetic composition includes an effective amount of the platelet-rich plasma as provided herein; or an effective amount of the wound or tissue healing composition as provided herein; and/or a cosmetically acceptable carrier.

In another aspect, methods of promoting skin regeneration in a scar, wrinkle or fat deficiency are provided. According to one embodiment, the cosmetic composition as described herein can be administered onto or into a scar, wrinkle or fat deficiency as a filler (e.g., rejuvenation material).

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur. For example, the phrase "optionally soaking the membrane" means that the soaking step may or may not be performed.

As used herein, "human birth tissue" encompasses one or more of the components of the placental organ including, but not limited to, the placental globe, the umbilical cord, the umbilical cord blood, the chorionic membrane, the amniotic membrane, the Wharton's jelly, the amniotic fluid, and other placental gelatins, cells, and extracellular material obtained from a seronegative, healthy human. As used herein, the term "human birth tissue material composition" refers to an allograft product formulated from human birth tissue; the term can include, for example, placental organ biomolecules or placental material in suspension produced by morselization or disruption of the placental organ or components of the placental organ. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof.

As used herein, the term "umbilical cord blood" encompasses the blood that remains in the placenta and the umbilical cord after childbirth.

As used herein, the term "platelet-rich plasma" refers to a human plasma concentrate rich in platelets prepared by any of the preparation techniques known to those skilled in the art.

As used herein, the term "effective amount" refers to an amount of a particular composition sufficient to elicit the desired therapeutic effects.

As used herein, the term "cosmetically acceptable carrier" refers to an intended cosmetically acceptable additional ingredient, such as a stabilizer, buffer, coloring agent, adjuvant, and the like.

A platelet-rich plasma composed of aseptically recovered umbilical cord blood. In one embodiment, the umbilical cord blood is of human origin is provided. A wound or tissue healing composition comprising an effective amount of the platelet-rich plasma as described herein admixed with an effective amount of a human birth tissue material composition is also provided. The human birth tissue material composition can comprise one or more of the components of the placental organ, including, but not limited to, placental globe, the umbilical cord, the chorionic membrane, the amniotic membrane, the amniotic fluid, and other gelatins, cells, and extracellular material of the placental organ.

The platelet-rich plasma of the present invention is derived from human umbilical cord blood obtained from a human placenta having an attached umbilical cord following childbirth from a seronegative, healthy female. Human birth tissue is preferably recovered from a full-term Cesarean delivery of a newborn. Alternatively, human birth tissue is recovered from a full-term vaginal delivery of a newborn. Potential human birth tissue donors providing informed consent are pre-screened during an examination of pre-natal medical records and blood test results. A comprehensive medical history and behavior risk assessment is obtained from the donor prior to donation, incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

The umbilical cord blood may be recovered by any methods known to those skilled in the art. In one aspect, the umbilical cord blood collection is performed after the infant has been delivered, but before delivery of the placenta (in utero). After the cord is clamped and the area of insertion is disinfected, the cord blood is collected by venipuncture (e.g., umbilical cord vein is cannulated using a needle connected to a blood bag). A closed collection system is used to reduce the risk of bacterial and maternal fluid contamination. The umbilical cord blood is collected by gravity, which usually takes approximately two to four minutes. The total time required for in utero cord blood collection by perinatal care providers is less than 10 minutes, and there is no requirement for extra personnel. In a second embodiment, ex utero cord blood collection is performed as soon as possible after delivery of the placenta. The ex utero cord blood collection is usually performed by dedicated trained personnel in a separate room, using a standard collection bag. The placenta is generally suspended on a specifically designed frame or stand and blood is collected by gravity from the most distant possible venipuncture site. The umbilical cord is cleaned with antiseptic solution, and the collection bag needle is introduced into the umbilical vein. Using either in utero or ex utero techniques for collection of umbilical cord blood, average cord blood unit volumes of 50 to 150 mL are commonly achieved.

Following collection, the umbilical cord blood may be cryopreserved by any methods known to those skilled in the art. For example, the umbilical cord blood may be cryopreserved in the liquid phase of liquid nitrogen using techniques described by Rubinstein et al (See Rubinstein P, Dobrila L, Rosenfield R E. Processing and cryopreservation of placental/umbilical cord blood for unrelated bone marrow reconstitution. Proc Natl Acad Sci USA 1995; 92:10119-22.). In one embodiment, the cryoprotectant is one commonly used in the industry, such as, for example, dimethyl sulfoxide (DMSO). In a preferred embodiment, the cryoprotectant is a control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. Any cryoprotectant specific to the umbilical cord blood described herein may be used. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

According to one aspect, the umbilical cord blood remains cryopreserved until just prior to use, at which time, the platelet-rich plasma is isolated using a commercially available platelet separation system. As such, the determination of which platelet separation system to use is largely dependent on the end-user (i.e., the medical professional administering the preparation). In an alternate embodiment, the platelet-rich plasma is isolated shortly after collection and remains cryopreserved until just prior to use. Currently, at least 16 commercial platelet separation systems are available, many of which vary significantly in the relative amounts of platelets, leukocytes, erythrocytes, and anabolic and catabolic growth factors. For example, the Arthrex ACP™ (Arthrex, Inc., Naples, Fla.) may be used as the platelet separation system, whereby 10 mL of umbilical cord blood yields approximately 3-5 mL of platelet-rich plasma. In another embodiment, the Biomet GPS III Platelet Concentrate System (Biomet Biologics, Inc., Warsaw, Ind.) may be used, whereby 27 mL of umbilical cord blood yields approximately 3 mL of platelet-rich plasma. Any commercially available or literature-based method of isolating platelets may be used (e.g., double-spin method; see de Mos M, van der Windt A E, Jahr H, et al. Can platelet-rich plasma enhance tendon repair? A cell culture study. Am J Sports Med. 2008; 36(6):1171-1178).

In a preferred embodiment, a wound or tissue healing composition is provided. The wound or tissue healing composition can include an effective amount of a platelet-rich plasma described herein admixed with an effective amount of a human birth tissue material composition. The birth tissue material composition may include one or more of the components of the placental organ. Exemplary placental organ components include the placental globe, the umbilical cord, the chorionic membrane, the amniotic membrane, the amniotic fluid, and other placental gelatins, cells, and extracellular material and combinations thereof. The composition can include a variety of placental organ components to aid in the healing cascade. In a preferred embodiment, the birth tissue material composition includes placental material in suspension produced by morselization or disruption of the placental organ or components of the placental organ. In one embodiment, the tissue may be morselized or otherwise rendered into fine particulates. Particles may be micron or submicron size ranges. In one embodiment, particle sizes may range from 1 micron to 100 microns. In another embodiment, particle sizes may range from 10 nm to 100 nm. In one embodiment, the human birth tissue material composition is recovered from the same donor from whom the platelet-rich plasma is derived. In an alternate embodiment, the human birth tissue material composition is recovered from a different donor from whom the platelet-rich plasma is derived.

In another aspect, the platelet-rich plasma described herein can be used alone, or in combination with one or more additional structural carriers, including, but not limited to, a placental membrane construct (e.g., amniotic membrane wound covering), a soft tissue allograft, a bone allograft (e.g., FDBA), or a birth tissue material composition as described herein. The platelet-rich plasma can be used alone, or in combination with one or more additional bioactive agents such as physiologically compatible minerals, growth factors, antibiotics, chemotherapeutic agents, antigen, antibodies, enzymes, vectors for gene delivery and hormones.

According to one embodiment, a method of treating a wound or defect is provided. The method includes the steps of preparing a platelet-rich plasma as described herein; or preparing a wound or tissue healing composition as described herein; and administering an effective amount of either the platelet-rich plasma or the wound or tissue healing composition onto or into the wound or defect. In one aspect, the wound includes a diabetic ulcer, decubitus ulcer, venous leg ulcer, arterial leg ulcer, cutaneous ulcer, or a wound arising on or around a soft tissue, connective tissue (e.g., cartilage, tendon, ligament), adipose tissue, bone, nerve, organ, vascular tissue, muscle, spinal cord, oral cavity, ocular surface, or a combination thereof. According to one aspect, the defect includes a soft tissue defect or bone void.

According to one embodiment, a method of promoting regeneration of a diseased or damaged tissue is provided. The method includes the steps of preparing a platelet-rich plasma as described herein; or preparing a wound or tissue healing composition as described herein; and administering an effective amount of either the platelet-rich plasma or the wound or tissue healing composition onto or into the diseased or damaged tissue. In one aspect, the diseased or damaged tissue includes, but is not limited to, soft tissue, connective tissue (e.g., cartilage, tendon, ligament), adipose tissue, bone, nerve, organ, vascular tissue, muscle, spinal cord, oral cavity, ocular surface, or a combination thereof.

The compositions and uses described herein are particularly useful in the treatment of: diabetic neuropathic ulcers or decubitus sores; bone and cartilage damage, such as deep joint cartilage or chondral damage (e.g., surgical repair of torn tendons); joint arthritis caused by trauma or aging; rotator cuff disorders; non-healing wounds (e.g., vasculitis); periodontal diseases; mesotherapy and/or mesotherapy injections; cardiac muscle damage such as in chronic cardiac failure, heart failure, ischemic and non-ischemic disorders, cardiomyopathy; gastro-oesophageal reflux disease; anal or urinary incontinence; hair loss; face-lift surgery (e.g., rhytidectomy); rhinoplasty; dermal fat grafts (e.g., in the treatment of facial augmentation); wound healing complications such as after eyelid blepharoplasty; corneal disorders, such as corneal opacity caused by chemical burns, affliction by Steven's Johnson syndrome and corneal ulcers; scarring of the cornea; dry eye syndrome; hematological diseases such as Thalassaemia; peripheral nerve damage, nerve suture and spinal cord injury; bone defects or disorders such as bone graft or bone fracture; skin damages or disorders such as acne (especially after dermabrasion treatment), burns, rubella or small pox scars, vitiligo, lipoatrophy, Kaposi's sarcoma, skin keloids or Dupuytren's palmar fibromatosis. The uses, methods and compositions according to the invention are useful in tissue healing, including bone regeneration and repair, mitogenesis, angiogenesis and/or macrophage activation.

In one aspect, a cosmetic composition is provided. The cosmetic composition includes an effective amount of the platelet-rich plasma as provided herein; or an effective amount of the wound or tissue healing composition as provided herein; and/or a cosmetically acceptable carrier. The cosmetic composition can be prepared according to the steps provided herein and combined with a carrier composition to formulate a cosmetic composition suitable for routine application to any part of the human skin to cease or reverse various signs of aging or to treat a particular skin condition or disorder. The cosmetic composition can be storage stable and color stable.

The cosmetically acceptable carrier can include any variety of components suitable for application to the human skin. According to one embodiment, the carrier composition includes one or more vitamins, minerals, proteins, fats, collagens (including collagen extracted from the placental globe), waxes, glycols and derivatives thereof, glycerols and derivatives thereof, oils (including essential oils), skin-abrading granules, fatty acids, cholesterols, alcohols, emollients, adsorbents, lubricants, moisturizing agents, emulsifying agents, thickening agents, humectants, surfactants, pharmaceutical ingredients, preservatives, antifungal agents, antioxidants, antimicrobial agents, structuring agents, dispersing agents, UV blocker and absorber ingredients (sunscreen), pH-adjusting components, sequestering or chelating agents, wetting agents and other components known in the art to be suitable for use in a cosmetic composition.

The cosmetically acceptable carrier can include other suitable components including, but not limited to, water, retinol, sorbitol, lanolin, beeswax, oleic acid, spermaceti, almond oil, egg oil, aloe, castor oil, tracacanth gum, clay, magnesia, talc, metal stearates, chalk, magnesium carbonate, zinc stearate, kaolin, glycerin, propylene glycol, polyethylene glycol, hyaluronic acid, chondroitin sulfate, elastin, polysaccharide, glycosaminoglycan, ascorbic acid, ascorbic acid derivatives, glucosamine ascorbate, arginine ascorbate, lysine or tyrosine ascorbate, gluthathione ascorbate, nicotinamide ascorbate, niacin ascorbate, allantoin ascorbate, creatine ascorbate, creatinine ascorbate, chondroitin ascorbate, chitosan ascorbate, DNA ascorbate, alpha hydroxyl acids, carnosine ascorbate, tocotrienol, rutin, quercetin, hesperedin, diosmin, mangiferin, mangostin, cyanidin, astaxanthin, lutein, lycopene, resveratrol, tetrahydrocurcumin, rosmarinic acid, hypericin, ellagic acid, chlorogenic acid, oleuropein, alpha-lipoic acid, niacinamide lipoate, gluthathione, andrographolide, carnosine, niacinamide, polyphenols, pycnogenol and mixtures thereof, benzophenones, benzotriazoles, homosalates, alkyl cinnamates, salicylates such as octyl salicylate, dibenzoylmethanes, anthranilates, methylbenzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof; antiacne agents such as salicylic acid; skin bronzing or tanning agent ingredients such as dihydroxyacetone, erytrulose, melanin; antioxidants such as vitamin C and derivatives thereof (e.g. ascorbyl acetate, ascorbyl phosphate and ascorbyl palmitate), vitamin A and derivatives thereof; folic acid and derivatives thereof; vitamin E and derivatives thereof such as tocopheryl acetate, flavons, or flavonoids, amino acids such as histidine, glycine, tyrosine, tryptophan, and derivatives thereof; carotenoids and carotenes; uric acid and derivatives thereof; citric acid, lactic acid, malic acid; stilbenes and derivatives thereof; and pomegranate extracts; vitamin K1 or K2, vitamin K1 oxide or vitamin K2 oxide, hormones, plant or botanical extracts, anti-inflammatory agents, concentrates of plant extracts, silicones, skin soothing ingredients, analgesics or anti-itch agents, skin penetration enhancers, solubilizers, alkaloids and processing aids; coloring agents including various dyes and pigments; perfumes or fragrances for the body; and other suitable components that do not interfere with the interaction between the platelet-rich plasma or the wound or tissue healing composition and the various layers of the human skin.

The cosmetically acceptable carrier is formulated in such a way that the combination of the platelet-rich plasma or the wound or tissue healing composition and the carrier are chemically compatible and do not form complexes which precipitate from the final cosmetic composition. According to one embodiment, the cosmetically acceptable carrier can be formulated as a cream, emulsion, lotion, gel, ointment, salve, butter, gel, putty, or balm. According to a preferred embodiment, the cosmetically acceptable carrier is a cream.

Various techniques known in the art may be utilized for preparing the cosmetic composition. According to one embodiment, the platelet-rich plasma or the wound or tissue healing composition and the cosmetically acceptable carrier as provided herein are mixed or blended according to a variety of conventional techniques. According to one embodiment, the platelet-rich plasma or the wound or tissue healing composition and the cosmetically acceptable carrier are mixed in a manner to produce a smooth and homogenous composition. According to one embodiment, the platelet-rich plasma or the wound or tissue healing composition as provided herein is introduced to the cosmetically acceptable carrier after the carrier is formed (i.e., post-added). In an alternative embodiment, the platelet-rich plasma or the wound or tissue healing composition is introduced during the cosmetically acceptable carrier preparation. The amount of platelet-rich plasma or wound or tissue healing composition present in the cosmetic composition can vary depending upon the chosen carrier, the frequency of use, and the severity of the skin defect or condition to be treated. According to one embodiment, the cosmetic composition includes from typically about 0.1% to about 99.0% platelet-rich plasma or wound or tissue healing composition based on total cosmetic composition weight. Optionally, a suitable amount of amniotic fluid components may also be combined with the cosmetically acceptable carrier. Bioactive agents such as physiologically compatible minerals, growth factors, antibiotics, chemotherapeutic agents, antigen, antibodies, enzymes, vectors for gene delivery and hormones may also be added to the cosmetically acceptable carrier. The amount of cosmetically acceptable carrier present in the final cosmetic composition can vary according to the final formulation of the cosmetic composition. According to one embodiment, the cosmetically acceptable carrier components can be present in an amount from typically about 0.1% to about 99.0% based on total cosmetic composition weight.

Methods of promoting skin regeneration in a scar, wrinkle or fat deficiency are provided. According to one embodiment, the cosmetic composition as described herein can be administered onto or into a scar, wrinkle or fat deficiency as a filler (e.g., rejuvenation material).

Methods of treating various signs of skin aging are also provided. According to one embodiment, the cosmetic composition as provided can be used for ceasing or reversing various signs of aging which include, but are not limited to, rhytids (e.g., crow's feet, marionette marks, neck bands, frown lines), elastosis (e.g., face and neck), pigmented spots, purpura, angiomas, general dryness, general itchiness, skin tags, warts, and dyschromia (hyperpigmentation or hypopigmentation).

Methods of treating a soft tissue defect or skin condition are also provided. For example, the cosmetic composition as provided herein can be used for sealing, molding, filling and/or otherwise treating a soft tissue defect on the skin of a patient. The skin condition can be caused by exposure to UV light, age, irradiation, chronic sun exposure, environmental pollutants, air pollution, wind, cold, heat, chemicals, disease pathologies, smoking, or lack of nutrition. Soft tissue defects that can be treated by the present cosmetic composition further include skin conditions such as, for example, ischemic wounds, scar revision or the treatment of traumatic wounds, severe burns, surgical wounds as well as treatment of cosmetic conditions (e.g., those involving repair or augmentation). Other skin conditions include, but are not limited to, keratosis, melasma, pruritus, spider veins, lentigo, dermatitis, psoriasis, folliculitis, rosacea, acne, impetigo, erysipelas, erythrasma, and eczema.

In use, the area of skin subject to application is initially washed and dried. A generous amount can then be placed on the fingertips or an appropriate delivery device such as a cloth or sponge. The composition can be dispensed in a spray, dollop, or liquid, aerosol, a fluid, or a semi-solid. The cosmetic composition may also be delivered in various consumer vehicles such as, for example, a lipstick, cleanser, toner, sunscreen, mask, bandage, foundation, or lotion. The cosmetic composition can then be applied onto the skin at the area to be treated. Optionally, the cosmetic composition can be rubbed into the skin using the fingertips. The cosmetic composition can be applied once or multiple times daily or as needed to repair a skin defect or condition or cease or reverse any signs of aging. The cosmetic composition can be applied to any part of the human skin in need including, but not limited to the facial skin, arm skin, leg skin, chest skin, abdomen skin, and back skin.

According to one embodiment, the platelet-rich plasma or other compositions described herein may be administered by a user (i.e., medical professional) either through injection or by direct application to the chosen site. Modes of administration include, but are not limited to, intramuscular, subcutaneous, intraperitoneal, percutaneous, soft tissue injection, intravenous, intravascular, intracerebral, transdermal, intraocular, topical or mucosal. Preferably, the platelet-rich plasma or other compositions described herein are readily syringable compositions. A single injection or multiple injections may be administered which can be to a single site or to more than one site in the subject to be treated. Multiple administrations may occur essentially at the same time or separated in time. The mode of administration, the dosage administered, and the dosage number will vary per individual depending on a variety of factors, including pharmacokinetic properties, patient conditions and characteristics, extent of symptoms, concurrent treatments, frequency of treatment and the desired effect. As described herein, the platelet-rich plasma or other compositions described herein can be formulated as a solid, semi-solid or liquid. Suitable formulations may include, but are not limited to, a cream, emulsion, spray, gel, ointment, salve, butter, gel, putty, balm, or pliable stick. In one embodiment, the gel or putty carrier could be achieved through collagen extracted from the placental globe.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A wound or tissue healing composition comprising:
   an effective amount of a platelet-rich plasma aseptically recovered from human umbilical cord blood; and
   an effective amount of a morselized human birth tissue material composition,
   wherein the platelet-rich plasma is admixed with the human birth tissue material composition to form the wound or tissue healing composition,
   wherein the human birth tissue is selected from the group consisting of placental globe, umbilical cord, chorionic membrane, amniotic membrane, Wharton's jelly, and other placental gelatins, other placental cells, and other extracellular material of the placental organ, and
   wherein the morselized human birth tissue material composition is not a single cell preparation.

2. The wound or tissue healing composition of claim 1, wherein the human birth tissue material composition is recovered from a same donor from whom the platelet-rich plasma is derived.

3. The wound or tissue healing composition of claim 1, wherein the wound includes a diabetic ulcer, decubitus ulcer, venous leg ulcer, arterial leg ulcer, cutaneous ulcer, or a wound arising on or around a soft tissue, connective tissue, adipose tissue, bone, nerve, organ, vascular tissue, muscle, spinal cord, oral cavity, ocular surface, or a combination thereof.

4. A method of treating a wound or defect comprising the steps of:
   administering an effective amount of the wound or tissue healing composition of claim 1 onto or into the wound or defect.

5. The method of claim 4, wherein the wound includes a diabetic ulcer, decubitus ulcer, venous leg ulcer, arterial leg ulcer, cutaneous ulcer, or a wound arising on or around a soft tissue, connective tissue, adipose tissue, bone, nerve, organ, vascular tissue, muscle, spinal cord, oral cavity, ocular surface, or a combination thereof.

6. The method of claim 4, wherein the defect is a soft tissue defect or bone void.

7. A method of promoting regeneration of diseased or damaged tissue comprising the steps of:
   administering an effective amount of the wound or tissue healing composition of claim 1 onto or into the diseased or damaged tissue.

8. The method of claim 7, wherein the diseased or damaged tissue is soft tissue, connective tissue, adipose tissue, bone, nerve, organ, vascular tissue, muscle, spinal cord, oral cavity, ocular surface, or a combination thereof.

9. A cosmetic composition comprising:
   an effective amount of the wound or tissue healing composition of claim 1; and,
   optionally, a cosmetically acceptable carrier.

10. A method for promoting skin regeneration in a scar, wrinkle or fat deficiency, comprising the steps of:
    administering an effective amount of the wound or tissue healing composition of claim 1 onto or into the scar, wrinkle or fat deficiency.

\* \* \* \* \*